United States Patent [19]
Kashiwagi et al.

[11] Patent Number: 5,336,698
[45] Date of Patent: Aug. 9, 1994

[54] BLOOD-COMPATIBLE MEDICAL MATERIAL

[75] Inventors: Nobuyoshi Kashiwagi, Saitama; Masatomi Sasaki, Kanagawa, both of Japan

[73] Assignee: Terumo Kabushiki Kaisha, Tokyo, Japan

[21] Appl. No.: 873,990

[22] Filed: Apr. 27, 1992

Related U.S. Application Data

[63] Continuation of Ser. No. 540,138, Jun. 19, 1990, abandoned.

[30] Foreign Application Priority Data

Jun. 21, 1989 [JP] Japan .................................. 1-159323

[51] Int. Cl.$^5$ ........................... A61F 2/00; C08L 1/00
[52] U.S. Cl. ........................... 523/113; 523/105; 523/112; 604/1; 604/66; 604/280
[58] Field of Search .............. 424/78, 422, 423, 78.08; 523/112, 113, 105; 604/1, 66, 280

[56] References Cited

FOREIGN PATENT DOCUMENTS

| | | |
|---|---|---|
| 0335972 | 2/1988 | European Pat. Off. . |
| 266795 | 5/1988 | European Pat. Off. . |
| 294905 | 12/1988 | European Pat. Off. . |
| 351314 | 11/1990 | European Pat. Off. . |
| 0126808 | 7/1983 | Japan . |

Primary Examiner—G. S. Kishore
Attorney, Agent, or Firm—Burns, Doane, Swecker & Mathis

[57] ABSTRACT

The invention provides a medical material in which biocompatibility is provided to a substrate stably for over an extended period of time because of the ability of the material to reduce or prevent undesirable physiological properties inherent in the substrate, such as blood clotting, activation of complement system, platelet adhesion and the like. Such abilities are effected by the bonding of a fatty acid and/or its derivative to the substrate through a polymer.

10 Claims, 2 Drawing Sheets

BLOOD-COMPATIBLE MEDICAL MATERIAL

This application is a continuation of Application Ser. No. 07/540,138, filed Jun. 19, 1990, now abandoned.

BACKGROUND OF THE INVENTION

This invention relates to a material for medical use, a process for its production and a medical device using the medical material. More particularly, it relates to a medical material which can be used under contact with blood and a medical device using the medical material. The medical material of this invention is adapted for use in, for example, artificial organs, dialyzers, blood filters, plasma separaters and indwelling catheters.

A variety of medical devices having blood-contacting members, such as artificial organs, have been developed and put into practical use. Biocompatibility is an important subject to be considered when a material for use in these medical devices is selected, and nature of the surface of a medical device to be used is an important factor with regard to the biocompatibility. On the contrary, it is needless to say that physical properties of such device are also of great importance. In consequence, it is an advantage in that a material which exhibits appropriate physical properties when applied to a medical device is firstly selected and then surface properties of the material are modified to improve its biocompatibility.

In fact, various methods for the improvement of surface properties have been proposed from such a point of view. For example, Japanese Patent Application Kokai No. 130069/1988 (EPA Publication Number 0335972, applicant, Terumo Corp.) discloses a method in which reactive terminal group of a fat-soluble vitamin or a fatty acid macromet having said reactive terminal group is bonded to a base material. This method was a landmark invention at that time in respect that biocompatibility was provided on the surface of a base material without spoiling excellent physical properties of the base as a material for medical use. The biocompatibility itself provided on the surface, however, is still insufficient for the purpose of applying the medical material to practical use, thus leaving a margin for further modification to improve the biocompatibility.

SUMMARY OF THE INVENTION

In view of the above, it therefore becomes an object to the present invention to overcome the above problems and to provide a new medical material having superior biocompatibility which can be maintained over an extended period of time and a process for manufacturing such material as well as a medical device making use of the same.

Particularly, in accordance with the present invention, there is provided a medical material comprising a substrate, a polymer having first and second classes of functional groups and a fatty acid and/or its derivative, wherein the polymer is bonded to the substrate and the fatty acid and/or its derivative is bonded to the polymer.

Also provided is a process for producing a medical material comprising the steps of bonding a functional group of the fatty acid and/or its derivative with the first class of the functional group of the polymer, and bonding the second class of the functional group of the polymer with a functional group of the substrate.

Preferably, the first class of the functional group of the polymer comprises carboxylic group and the second class of the functional group of the polymer comprises epoxy group.

In addition, in accordance with the present invention, there is provided a medical device used under contact with blood wherein part of the device in contact with the blood comprises a medical material which comprises a substrate, a polymer and a fatty acid and/or its derivative wherein the polymer is bonded to the substrate and the fatty acid and/or its derivative is bonded to the polymer. Other objects and advantages of the present invention will[be made apparent as the description progresses.

DETAILED DESCRIPTION OF THE INVENTION

The following describes the present invention in detail.

The material for medical use in accordance with the present invention comprises a substrate and a high polymer derivative immobilized thereon, wherein the high polymer derivative comprises bonding a fatty acid and/or its derivative with a polymer. In other words, in the material for medical use according to the present- invention, a fatty acid and/or its derivative is bonded to a substrate but indirectly through a polymer. In consequence, a great number of fatty acids are able to be fixed per one bonding point the substrate, thus creating superior biocompatibility which, because release of fatty acids may not occur, is stable over an extended period of time.

Fatty acids having superior biocompatibility, especially blood-compatibility, are used in the present invention as ligands. Illustrative examples of fatty acids as eligible ligands for purposes of the present invention include unsaturated fatty acids such as elaidic acid, oleic acid, linoleic acid, linolenic acid, arachidonic acid and eicosapentaenoic acid and saturated fatty acids such as lauric acid, myristic acid, pentadecylic acid, palmitic acid, stearic acid and the like, most preferable fatty acid being linoleic acid because of its excellent compatibility with the blood. In the practice of the present invention, these fatty acids may be used alone or as a mixture of two or more.

These ligands may preferably be in the form of a fatty acid derivative having a spacer, preferably a hydrophilic spacer, for the purpose of improving the blood-compatibilityWhen a fatty acid derivative is applied to the material for medical use, an effect to prevent platelet adhesion can be expected due to the presence of a molecular chain (a spacer) between a fatty acid moiety and a copolymer. Such an effect may provide further improved biocompatiDility, and easy control of the length of such a molecular chain may provide a stable flexibility of the material.

Illustrative examples of the spacer are alkylene glycol derivatives having highly reactive functional groups on both terminal ends, preferably those having amino groups, such as polyethylene glycol diamine, polypropylene glycol diamine and polytetramethylene glycol diamine. For example, when a spacer has alkylene glycol units, the degree of polymerization depends on the kind of alkylenes to be used, but is preferably about 1 to 100. As the alkylene glycol unit, polyethylene glycol and polypropylene glycol are preferable, more preferably a polyethylene glycol with its degree of polymerization being 20 to 90 and a polypropylene glycol with its polymerization degree being 10 to 50.

The polymer for use in the present invention has a molecular weight of 500 to 500,000, preferably 5,000 to 300,000 more preferably 10,000 to 100,000, and may be a polymer having the first class functional groups which have the bonding ability to the above-described fatty acid and/or its derivative and the second class functional groups which have the bonding ability to the substrate that will be described later in detail. Effects of the polymer can be exhibited sufficiently within this range of the molecular weight, even if the number of its binding points to the substrate is small because of the large surface area of the polymer to be bonded with the substrate. Molecular weights of less than 500 will result in insufficient covering of the surface of the substrate, and those of more than 500,000 will not be practicable because of low solubility of the polymer and its low reactivity with the surface of the substrate.

The first and the second classes of functional groups of the polymer eligible for purposes of the present invention are epoxy group, carboxylic group, aldehyde group, amino group and the like. These first and second classes of functional groups may be the same or different, respectively. A glycidyl ester of (meth)acrylic acid and a glycidyl ester of vinyl compound are preferable as material monomers having epoxy group for use in the polymer, and (meth)acrylic acid and vinyl acetate are preferable monomers having carboxylic group for use in the polymer. For the purpose of synthesizing a polymer having a given composition of epoxy and carboxylic groups, esters such as an ester of (meth)acrylic acid, vinyl acetate and methyl (meth)acrylate, ethyl (meth)acrylate, propyl (meth)acrylate, isopropyl (meth) acrylate, butyl (meth)acrylate, isobutyl (meth)acrylate, hydroxymethyl (meth)acrylate, hydroxyethyl (meth)acrylate, propylene, butylene, pentene, vinyl alcohol, vinyl glycidyl ether and the like or mixtures thereof may be used as the material monomer.

The polymer of the present invention may have either one or two or more classes of functional groups. If the polymer has at least two classes of functional groups, its bonding capacities with the fatty acid and/or its derivative and with the substrate can be controlled easily by changing the number of the functional groups of each class. Most preferred are a glycidyl (meth)acrylate copolymer having epoxy groups and a glycidyl (meth)acrylate-(meth)acrylic acid copolymer having both carboxylic and epoxy groups.

In the case of the polymer having epoxy groups, the ratio of epoxy group-containing monomers in the polymer, as the amount of glycidyl (meth)acrylate in the (meth)acrylate copolymer, may preferably be within the range from 0.01 to 60% by weight. Weight ratios of epoxy group-containing monomers exceeding 60% by weight are not preferable because gelation is apt to occur at such high ratios during polymerization. The copolymer may suffice its minimum function when it contains at least one molecule of an epoxy group-containing monomer, but 0.01% by weight or higher in terms of the weight ratio is preferable for the purpose of improving surface properties.

The substrate of the present invention is used as the base material of the medical material. Cellulose and its derivatives may most preferably be used. Also usable are polyvinyl alcohol, partially saponified polyvinyl acetate, copolymer of ethylenevinyl alcohol, partially saponified copolymer of ethylenevinyl acetate, polyacrylic acid or polymethacrylic acid and copolymer thereof, polyhydroxyethylmethacrylate, chitin, chitosan, collagen, polyacryl amide and the like. The substrate may be used in various forms of molded materials such as membrane, hollow fiber, fiber and the like.

Process for the production of the medical material of the present invention is not specifically limited but may preferably be performed by the following manner.

The process, in accordance of the present invention, comprises the steps of bonding a functional group of a fatty acid and/or its derivative with a functional group of a polymerizable material, and bonding a functional group of said polymerizable material with a functional group of a substrate.

These steps may be performed either simultaneousy or in a given order. For example, in the case of the use of an epoxy group-containing polymer and a fatty acid and/or its derivative having amino group on the terminal end, the polymer and the fatty acid (or its derivative) are made into the form of a high polymer derivative by means of graft-copolymerization through the epoxy group of the polymer. In the same manner, the polymer containing both epoxy and carboxylic groups and a fatty acid derivative having amino group on the terminal ends are made into a high polymer derivative by graft-copolymerization through the carboxyl group of the polymer. These reactions may be performed by commonly used means.

Especially, when a polymer has epoxy groups as the functional group, a fatty acid and/or its derivative having functional groups which can react with epoxy group, such as carboxylic group and amino group, may firstly be subjected to reaction, bonding or graft-copolymerization with a portion of epoxy groups of the polymer and then the remaining epoxy group of the polymer may be allowed to react with functional groups of a substrate.

Introduction of epoxy group into a polymer may be achieved by reacting glycidyl (meth)acrylate with a polymerizable material in the presence of an initiator such as ammonium cerium nitrate, hydrogen peroxide-ferrous salt complex or the like.

Introduction of epoxy and carboxylic groups into a polymer may be achieved by reacting glycidyl (meth)acrylate and methacrylic acid with a polymerizable material in the same manner.

The polymer for use in the present invention can be obtained by commonly used industrial methods such as water suspension polymerization, emulsion polymerization, mass polymerization, solution polymerization and the like.

Bonding reaction of a high polymer derivative with a substrate which is a high polymer compound may be performed by firstly dissolving the high polymer derivative in an appropriate organic solvent, such as acetone, methyl ethyl ketone, dioxane or tetrahydrofuran, and then adding to the resultant solution a Lewis acid catalyst, a basic catalyst and the high molecular weight compound.

Lewis acid catalysts eligible for purposes of the present invention include boron trifluoride, stannic tetrachloride, zinc chloride and the like. Boron trifluoride is most preferable in view of its high reactivity.

Basic catalysts eligible for purposes of the present invention are hydroxides of some of the alkaline earrib metals such as calcium, strontium, barium and radium, and alkali metal hydroxides including lithium hydroxide, sodium hydroxide, potassium hydroxide, rubidium hydroxide, cesium hydroxide and francium hydroxide. Sodium hydroxide is most preferable in view of its high solubility and reactivity.

Various formed products such as membrane, hollow fiber, fiber and the like may also be used as the substrate of the present invention. In such a case, the reaction is performed by soaking the molded material into a solution of a high polymer derivative and the above-described catalysts.

The thus obtained reaction product is possessed of biocompatibility. When a formed product is used as the substrate of the high polymer derivative, biocompatibility can be provided to the product by changing only its surface properties without spoiling physical properties inherent in the product. In other words, undesirable physiological properties inherent in the substrate, which cause blood clotting, activation of immune system, platelet metamorphosis and the like, can be reduced or eliminated. In consequence, the medical material in accordance with the present invention is preferably used under contact with blood, and can be applied as blood-contacting members to various medical devices such as, for example, artificial organs, dialyzers, blood filters, plasma separaters and indwelling catheters.

EXAMPLES

Examples of the present invention are given below by way of illustration but not by way of limitation.

EXAMPLE 1

Preparation of linoleic acid derivative

A flask was charged with 20.0 g of linoleic acid which has been dissolved in advance in 70 ml cf water-free benzene, and the air in the flask was purged with nitrogen gas. To this was added 14.8 g of phosphorus pentachloride gradually in five steps. The mixture was stirred for 12 hours at room temperature and then refluxed for an additional 2 hours. Thereafter, benzene and phosphoryl trichloride and hydrogen chloride as the by-products were distilled off and the remaining portion was subjected to distillation under reduced pressure to obtain 14.0 g of linoleic acid chloride (boiling point, 155° C./1.5 ramrig; yield, 76%).

A 3.66 g portion of the linoleic acid chloride thus obtained was dissolved in 70 ml of dichloromethane and the solution was added dropwise into a flask which has been charged in advance with 50.4 g of polyethylene glycol diamine (marketed by Toray Industries, Inc. under the trade mark of PGD-40; molecular weight, 4,114), 1.48 g of triethylamine and 120 ml of dichloromethane. After completion of the dropwise addition of the solution spending 30 minutes under nitrogen atmosphere at 0° C., the resultant mixture was stirred for an additional 2 hours gradually increasing the temperature to room temperature to complete the reaction. Thereafter, triethylamine hydrochloride as a by-product of the reaction was removed by filtration, triethylamine and dichloromethane were distilled off and the remained portion was dissolved in 100 ml of chloroform and the resultant solution was mixed gently with 100 ml of water to wash the product. Organic solvent layer was separated from the mixture and concentrated after removing water in the layer with the aid of sodium sulfate anhydride. The concentrated product was purified by means of High Performance Low Pressure Liquid Chromatography System (FMI-C) using Wako gel C-300 and an eluent system of chloroform/methanol (9/1 by volume ratio) to obtain 13.7 g of purified product with a yield of 26%.

Structure of the purified product was determined by means of infrared spectrophotometry (IR method) and proton nuclearmagnetic resonance method (1H-NMR method), and the absence of linoleic acid and PGD-40 in the product was confirmed by means of liquid chromatography (GPC mode; eluent, THF). Results of characteristic values obtained by these methods are listed below.

IR method:

Stretching vibration of amide carbonyl: 1650 cm$^{-1}$;
Deformation vibration of amide NH: 1540 cm$^{-1}$;
Stretching vibration of ether CO: 1100 cm$^{-1}$ 1H-NMR method:

—C$\underline{H}_3$ in linoleic acid: $\delta=0.9$ ppm;
—C$\underline{H}_2$ in linoleic acid: $\delta=1.3$ ppm;
—OC$\underline{H}_2$—C$\underline{H}_2$O—in polyethylene glycol: $\delta=3.7$ ppm;
—C$\underline{H}$=C$\underline{H}$—in linoleic acid olefin bond: $\delta=5.3$ ppm GPC method:

Retention volume of purified product: 11.4 ml;
Retention volume of PGD-40: 12.6 ml;
Retention volume of linoleic acid; 15.1 ml

EXAMPLE 2

Preparation of copolymer

A glass tube was charged with azobisisobutyronitrile as a polymerization initiater, methyl methacrylate, glycidyl methacrylate, 3-methacryloxypropyl-tris (methoxyethoxy) silane (produced by Chisso Corp.) and methacrylic acid, with the weight ratio of 0.15/7.5/15/6/1.5. After the contents in the tube were cooled and solidified with the aid of liquid nitrogen, the tube was subjected to degasification using a vacuum pump, charged with nitrogen gas, subjected again to degasification and then sealed up. The thus sealed tube was heated in a constant temperature bath at a predetermined temperature for a predetermined time as exemplified in Table 1. Thereafter, the tube was cooled off and unsealed, the contents were dissolved in tetrahydrofuran and the resultant solution was subjected to methanol precipitation to obtain a white polymer product.

The same process was repeated except that methacrylic acid was not used and, instead, the weight ratio of 3-methacryloxypropyl-tris(methoxyethoxy) silane was changed from 6 to 7.5.

These copolymers thus obtained were dissolved in methyl ethyl ketone and titrated with 0.01N perchloric acid/acetic acid solution using ethyltrimethylanunoniumbromide as a catalyst and Crystal Violet as an indicator in order to determine their epoxy equivalents from which glycidyl methacrylate contents were calculated. The results are shown in Table 1.

TABLE 1

| Charged monomers | Copolymer No. | Polymerization temp. (°C.) | time (min) | Glycidyl methacrylate content (wt %) |
|---|---|---|---|---|
| A | 1 | 60 | 50 | 52.9 |
| B | 2 | 60 | 50 | 52.7 |

A: MMA/GMA/MPTMS/MA = 7.5/15/6/1.5 (weight ratio)
B: MMA/GMA/MPTMS = 7.5/15/7.5 (weight ratio)
MMA: methyl methacrylate
GMA: glycidyl methacrylate
MPTMS: 3-methacryloxypropyl-tris(methoxyethoxy)silane
MA: methacrylic acid

EXAMPLE 3

Reaction of linoleic acid derivative with copolymer No. 1 (Preparation of high polymer derivative I)

A flask was charged with 4.00 g of the copolymer No. 1 obtained in Example 2, 0.718 g of dicyclohexyl carbodiimide and 100 ml of a solvent system of tetrachloromethane and acetonitrile (1:1 in volume ratio), the air in the flask was purged with nitrogen gas and the mixture was stirred at room temperature for 60 minutes. Then a 12.0 g portion of the linoleic acid derivative obtained in Example 1, which has been dissolved in advance in 20 ml of a solvent system of tetrachloromethane and acetonitrile (1:1 in volume ratio), was added dropwise gradually to the above mixture and the stirring was continued for 60 minutes at room temperature and for an additional 60 minutes at 60° C. Thereafter, the contents in the flask were cooled to room temperature and filtered through a glass filter. When solvents in the filtered solution were distilled off to a slight degree, a yellow and highly viscous crude product was obtained.

The thus obtained crude product was mixed with 200 ml of methanol and stirred at room temperature for about 30 minutes to make the product into suspension. Then the suspension was centrifuged and resulting supernatant fluid was removed by decantation. This suspension/centrifugation process was repeated twice more and then subjected to vacuum drying to obtain 9.63 g of a high polymer derivative I.

EXAMPLE 4

Reaction of linoleic acid derivative with copolymer No. 2 (Preparation of high polymer derivative II)

A flask was charged with 3.00 g of the copolymer No. 2 obtained in Example 2, 10.0 g of the lit:oleic acid derivative obtained in Example 1 and 80 ml of a solvent system of benzene and THF (4:3 in volume ratio), the air in the flask was purged with nitrogen gas and the mixture was subjected to reflux for 3 hours. Thereafter, the reacted contents in the flask were cooled to room temperature. When the solvent in the mixture was distilled off to a slight degree, a yellow and highly viscous crude product was obtained.

The thus obtained crude product was mixed with 100 ml of methanol and stirred at room temperature for about 130 minutes to make the product into suspension. Then the suspension was centrifuged and resulting supernatant fluid was removed by decantation. This suspension/centrifugation process was repeated twice more and then subjected to vacuum drying to obtain 8.71 g of a high polymer derivative II.

EXAMPLE 5

Reaction of linoleic acid with copolymer No, 2 (Preparation of high polymer derivative III)

A flask was charged with 0.90 g of linoleic acid together with a mixture of 0.04 g of pyridine anti 30 ml of water-free dioxane, the air in the flask was purge with nitrogen gas and the mixture was stirred at 80° C. for 30 minutes. The flask. was then charged with 3.00 g of the copolymer No. 2 obtained in Example 2 after dissolving the copolymer in 70 ml of water-free dioxane and the mixture was stirred for an additional 6 hours at 80° C. Thereafter, the reacted contents in the flask were cooled to room temperature. When the solvent in the mixture was distilled off to a slight degree, a pale brown and highly viscous crude product was obtained.

The thus obtained crude product was mixed with 100 ml of methanol and stirred at room temperature for about 30 minutes to make the product into suspension. Then the suspension was centrifuged and resulting supernatant /fluid was removed by decantation. This suspension/centrifugation process was repeated twice more and then subjected to vacuum burying to obtain 3.05 g of a high polymer derivative III.

EXAMPLE 6

Bonding or graft-copolymerization of high polymer derivatives to regenerated cellulose film Each of the high polymer derivatives I, II and III obtained in Examples 3, 4 and 5, respectively, was immobilized on the surface of a regenerated cellulose film by means of graft-copolymerization as follows.

A 0.3 g portion of a regenerated cellulose film (0.2 mm in thickness) was immersed for 30 minutes in a 100 ml aqueous solution of 0.5% (weight per volume) sodium hydroxide. The cellulose film was then removed from the solution and immersed again in an acetone solution containing 0.5% (weight per volume) of one of the high polymer derivatives Z, II and III for 24 hours at room temperature to complete the polymerization reaction. Thereafter, the cellulose film was removed from the acetone solution and rinsed thoroughly with acetone, ethanol and distilled water in that order.

In this manner, medical materials I, II and III were obtained and used as samples in the following Example 7.

COMPARATIVE EXAMPLE 1

As for Comparative Example 1, a sample of untreated regenerated cellulose film was prepared.

COMPARATIVE EXAMPLE 2

As for Comparative Example 2, linoleic acid derivative-treated regenerated cellulose film was obtained as follows.

A four neck flask was charged with 7.5 ml of water-free dioxane and 0.611 g of pyridine, the air in the flask was purged with nitrogen gas and then 2.1094 g (0.0075 mol) of linoleic acid was added in the flask. The mixture was stirred at 100° C. for 30 minutes. Thereafter, the flask was charged with 16.65 g (0.014 mol) of polyethylene glycol glycidyl ether after dissolving the ether in 30 ml of water-free dioxane and the mixture was stirred at 100° C. Progress of the reaction was traced by dissolving 50 μl portion of the reaction mixture in 2 ml of tetrahydrofuran and subjecting 10 μl portion of the dissolved sample to HPLC analysis. The reaction was stopped when the reaction ratio reached 94.4% (5 hours after commencement of the reaction).

Conditions applied to the HPLC analysis were:

Column; Combination of Shodex GPC KF-801 and Shodex GPC KF-802 (both from Showa Denko K.K.)

Solvent; tetrahydrofuran

Flow rate; 1 ml/min

Detectors; UV analyzer (detection wave, 210 nm) and differential refractometer

After completion of the reaction dioxane was removed from the reaction system under vacuum,, the resultant contents were mixed with 200 ml of hexane and stirred thoroughly, ana then the mixture was centrifuged at 3000 rpm for 10 minutes to remove supernatant fluid. This process was repealed again and the resultant pellet was mixed with 120 ml of ether and stirred thoroughly. The mixture was then centrifuged at 3000 rpm for 10 minutes and the supernatant fluid (first ether extract) was transferred into a new centrifugation tube. The remaining pellet was again subjected to the same ether extraction process and the second ether extract was added to the first extract. The totalled extract was cooled with tap water to form precipitates, centrifuged at 3000 rpm and at 0° C., and the resultant pellet was vacuum-dried. Formation of expected product was confirmed by subjecting the dried product to epoxy equivalent measurement and IR, NMR and HPLC analyses, The yield was found to be 35.4%.

The linoleic acid derivative thus obtained was immobilized on the surface of a regenerated cellulose film as follows.

A 0.3 g portion of a regenerated cellulose film (0.2 mm in thickness) was immersed for 30 minutes in a 100 ml aqueous solution of 0.5% (weight per volume) sodium hydroxide. The cellulose film was then remove from the solution and immersed again in a dioxane solution containing 0.5 (weight per volume) of the linoleic acid derivative for 24 hours at room temperature. Thereafter, the cellulose film was removed from the dioxane solution, rinsed thoroughly with distilled water and used as a sample for comparative experiments.

EXAMPLE 7 AND COMPARATIVE EXAMPLES

Evaluation tests 1 and 2 were performed as follows using the medical materials I, II and III obtained in Example 6, Comparative Examples 1 and 2 Results of the evaluation tests 1 and 2 are shown in Tables 2 and 3, respectively.

EVALUATION TEST 1 (PLATELET METAMORPHOSIS TEST)

A predetermined amount of venous blood was collected from a healthy person using a polypropylene syringe containing 3.8% sodium citrate solution (1:9 volume ratio to the blood to be collected), the collected blood sample was transferred into a polypropylene tube by letting the blood flow down gently on the inner surface of the tube and then the blood-containing tube was centrifuged at 800 rpm for 5 minutes. The resulting supernatant fluid as platelet rich plasma (PRP) was diluted with a diluted solution of the 3.8% sodium citrate solution (diluted one-tenth by volume with lactate Ringer solution ) to obtain a platelet suspension. The number of platelets in the thus prepared suspension was estimated to be 66,000 /mm$^3$.

A 0.2 ml portion of the platelet suspension was dropped on each sample of the high polymer derivative-treated regenerated cellulose films (1 cm$^2$ in size for each film) obtained as the medical material I, II and III in Example 6, as well as on a sample of untreated regenerated cellulose film (1 cm$^2$ in size) for use in Comparative Example 1 and a sample of linoleic acid derivative-treated regenerated cellulose film (1 cm$^2$ in size) for use in Comparative Example 2. Such a volume of the platelet suspension was used in order to make its thickness into 2 mm on the film sample. After contacting the platelet suspension with film samples for 30 minutes at room temperature, each film sample was washed lightly with the diluted sodium citrate solution and then immersed in a lactate Ringer solution containing 2.5% glutaraldehyde for a whole day and night at a cool place in order to fix the platelets on the film. Thereafter, the film was washed lightly with the diluted sodium citrate solution, alehydrated with ethanol, air-dried and then subjected to the observation of platelet metamorphosis using a scanning electron microscope (JSM-840, manufactured by JEOL Ltd.). The dehydration process was performed in stepwise manner by treating the film with 50%, 60%, 70%, 80%, 90%, 95%, 100% and additional 100% solution of ethanol in that order, each step being performed for 10 minutes. Results of the electron microscopic observation were evaluated on the basis of the number of platelets adhered to the film within the area of 0.07 mm$^2$ as well as their morphological changes by classifying the changes into the following three types Type I: Metamorphosis of a platelet from its normal discus form into a spherical form with the formation of 3 to 4 pseudopodia. This type of platelet is considered to have relatively weak adhesion ability to the surface of the film material.

Type II: Formation of several pseudopodia, with up to half the length of each pseudopodium from its base being expanded. This type of platelet is considered to have a strong adhesion ability to the surface of the film material.

Type III: More than half the length of each pseudopodium expands into thin cellular form started at its base and thus expanded basal parts of pseudopodia cover the platelet body almost completely, making the whole body into a pseudo-circular form in appearance. This type of platelet is considered to have complete adhesion ability to the surface of the film material.

Results of the evaluation are shown in Table 2.

TABLE 2

| Samples | Platelet morphology (% ratio) | | | Adhered platelets (Numbers/ /0.07 mm$^2$) |
|---|---|---|---|---|
| | Type I | Type II | Type III | |
| Inventive Example 1*$^1$ | 67.7 | 29.0 | 3.2 | 62 |
| Inventive Example 2*$^2$ | 68.3 | 28.0 | 3.7 | 82 |
| Inventive Example 3*$^3$ | 74.2 | 18.1 | 7.6 | 105 |
| Comparative Example 1*$^4$ | 48.9 | 37.5 | 13.7 | 352 |
| Comparative Example 2*$^5$ | 110 | 88.2 | 3.6 | 112 |

*$^1$Medical material I; *$^2$Medical material II; *$^3$Medical material III; *$^4$untreated regenerated cellulose; and *$^5$linoleic acid derivative-treated regenerated cellulose.

EVALUATION TEST 2 (CHANGES IN THE COMPLEMENT ACTIVITY)

Changes in the complement activity in blood serum originated from the medical materials I, II and III obtained in Example 6, Comparative Examples 1 and 2 were measured in accordance with the Mayer's original method as follows.

Each sample of the medical materials was immersed in physiological saline solution to make it into a state of sorption equilibrium. The equilibrated sample was cut into a piece of 20 cm$^2$ after removing moisture on its surface lightly, and the piece was transferred into a plastic tube. The tube was charged with 1 ml of blood serum obtained from an adult dog and then incubated at 37° C. for 3 hours to activate the reaction system. Thereafter, changes in the complement activity $CH_{50}$ (50% hemolytic unit of complement) were measured and decreasing rate of the activity was calculated. Results are shown in Table 3.

TABLE 3

| Samples | Decrease in $CH_{50}$ (%) |
| --- | --- |
| Inventive Example 1 (medical material I) | 13.7 |
| Inventive Example 2 (medical material II) | 12.4 |
| Inventive Example 3 (medical material III) | 16.0 |
| Comparative Example 1 (regenerated cellulose) | 38.0 |
| Comparative Example 2 (linoleic acid derivative-treated regenerated cellulose) | 25.0 |

As is evident from Table 3, decrease in the complement activity ($CH_{50}$) in blood serum is remarkably small in the case of the medial material (cellulose sheet) of the present invention compared to the untreated cellulose sheet.

EXAMPLE 8 AND COMPARATIVE EXAMPLE 3

A dialyzer was prepared in the following manner.

A bundle of hollow fibers made of cellulose regenerated by means of cuprammonium process were put in a glass tube.

One end of the tube was immersed in 0.5% (w/v) aqueous solution of NaOH and the inside of hollow fibers were filled, with the NaOH solution with the aid of an aspirator equipped on the other end of the tube. After standing still for 30 minutes at room temperature, the NaOH solution filled in the hollow fibers was removed and replaced by a 0.5% (w/v) solution of the medical material I dissolved in dioxane with the aid of the aspirator in the same manner described above, and the tube was kept at room temperature for 24 hours to immobilize the medical material to the cellulose hollow fibers . After removing the solution, inside of the tube was washed with dioxane followed by thorough washing with acid and distilled water and then dried by blowing air at 25° C. through the tube with the aid of the aspirator. The tube was further kept overnight in an oven at 60° C. to complete the drying The following describes the dialyzer of the present invention in detail using a partially cutaway perspective view of a module for extracorporeal circulation experiment use which is shown in FIG. 1.

Figure 1:
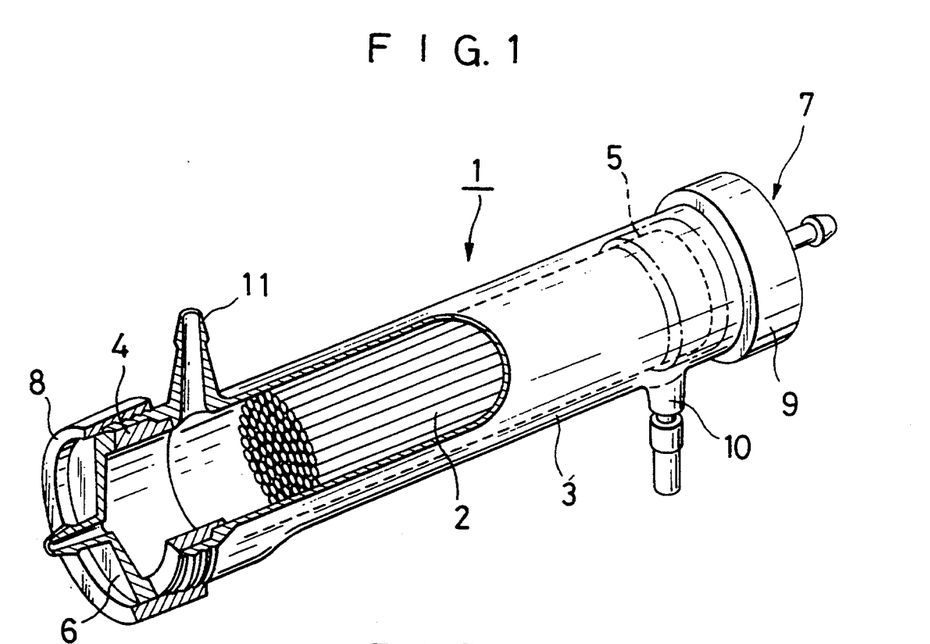
FIG. 1 is a partially cutaway perspective view of a module of a dialyzer used in Example 8 and Comparative Example 3 for extracorporeal circulation experiments.

A total of 34 1 hollow fibers made cf cellulose which has been regenerated by means of cupraponium process, each fiber having its inside diameter of about 200 μm outside diameter of about 224 μm and effective length of 14 cm, were made into a bundle as indicated by the numeral 2 in FIG. 1. The bundle 2 was inserted into a cylindrical main body 3. Both ends of the cylindrical main body 3 were then fixed with polyurenhane pottings 4 and 5, equipped with headers 6 and 7 and sealed with caps 8 and 9 in that order. Inlet and outlet tubes 10 and 11, respectively, were established at sites close to DOtH ends of the cylindrical main body 3 for use in the circulation. of dialysis solution The dialyzer I (artificial kidney) was prepared in this way. Total inner area of the cellulose film was estimated to be 300 cm$^2$.

The dialyzer thus prepared was then filled with distilled water and sterilized for 30 minutes at a temperature of 115° C. using an autoclave, for use in the following evaluation test.

EVALUATION TEST 3 (EXTRACORPOREAL CIRCULATION TEST)

A rabbit was fixed at a supine position on a Kitajima's fixing plate. Its hair within the operation area was cut using a pair of electromotive hair clippers and the naked area was cleaned up with ethanol-soaked cotton. Median incision from just below the mandible to the clavicle was performed using a pair of scissors, followed by the incision of epimysium in order to separate right (left) pare or column carotid artery taking care not to damage nerves, branched blood vessels and peripheral tissues. Next, left (right) part. of facial vein was deeply separated taking the same care . Into this was inserted an indwelling catheter (SURFLO, trademark for an indwelling catheter manufactured by Terumo Corporation) which was equipped with a rubber cap for admixture use of physiological saline solution containing 1 IU/ml of heparin, and the catheter was then fixed by ligation.. The above-described common carotid artery was also fixed with the indwelling catheter in the same manner.

Figure 2:
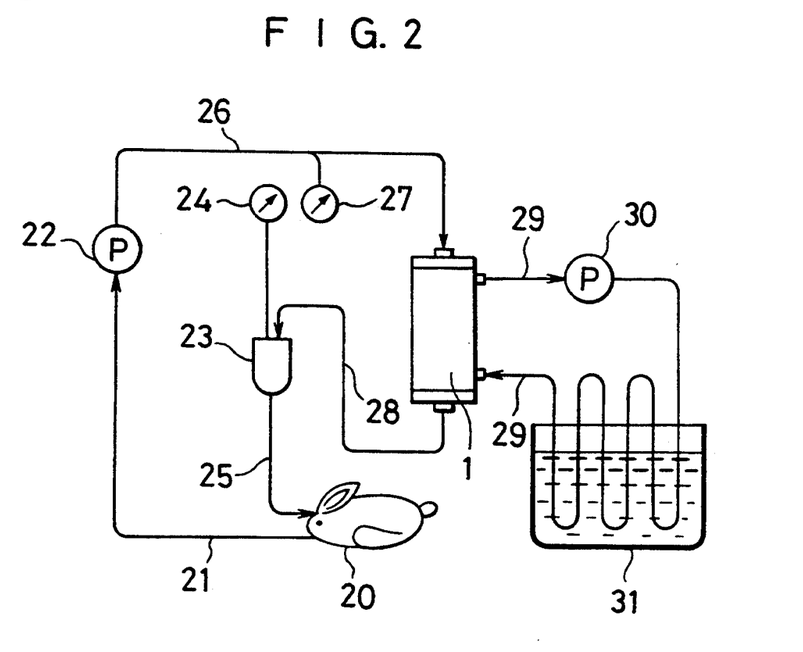
FIG. 2 is a flow sheet of experiments performed in Example 8 and Comparative Example 3.

An experimental system was established as shown in FIG. 2, by using thus prepared rabbit as indicated by the numeral 20 in FIG. 2 and the above-described dialyzer. Also, a dialyzer comprising a bundle of hollow fibers made of cellulose regenerated by means of cuprammonium process, having almost the same total inner area of the cellulose film as that of the inventive dialyzer but excluding the treatment process with the medical material of the invention, was used as a control (Comparative Example 3) . As shown in FIG. 2, a catheter 21 connected with an artery of the rabbit 20 was further connected with a pump 22, and a chamber 23 and a vein of the rabbit 20 were communicated each other through a catheter 25. The pump 22 and the dialyzer 1 were communicated each other through a tube 26 which was further connected with an inlet 27 of a manometer. The dialyzer 1 and the chamber 23 which was connected with an outlet 24 of the manometer were communicated each other through a tube 28. On the other hand, the inlet and outlet of the dialyzer 1 for use in the circulation of dialysis solution were connected with a tube 29 and the tube 29 was equipped with a pump 30 and immersed a water bath 31 controlled at a temperature of 37° C. The thus established passages for the circulation of blood and dialysis solution were washed with 100 ml of physiological saline solution containing 1 IU/ml of heparin for priming.

Extracorporeal circulation was performed at a blood circulation rate of 10 ml/min. Anticoagulation agents were excluded completely from the circulation conditions. A 1 ml potion of blood sample was collected immediately after the commencement of the extracorporeal circulation as well as at predetermined intervals of 5, 10, 15, 20, 30, 45, 60 and 120 minutes during the circulation experiment. Blood cell counting in each of the blood samples thus collected was performed using a blood cell counter (ELT-8, manufactured by Ortho Instrument) after subjecting the samples to anticoagulation treatment with physiological saline solution containing 1.5% of Na2-EDTA.

Results thus obtained, including white blood cell count (WBC), platelet count (PLT) and hematocrit value (HCT), are shown in Tables 4 and 5. Table 4 shows data obtained from an experiment using the inventive dialyzer comprising a bundle of hollow fibers made of cellulose regenerated by means or cuprammonium process which have been treated with the medical material I obtained in Example 6, and Table 5 shows data obtained from a comparative experiment (Comparative Example 3) using the same dialyzer but without introducing the medical material. White blood cell count and platelet count were expressed as corrected counts based on the Ht value just before the commencement of the entracorporeal circulation using the following formula.

$$Cx = Co \frac{Htx}{Hto}$$

where Cx is corrected count, Co is measured count, Htx is standard Ht value for the correction (initial Ht value) and Hto is Ht value at the time of Co measurement.

Figure 3:
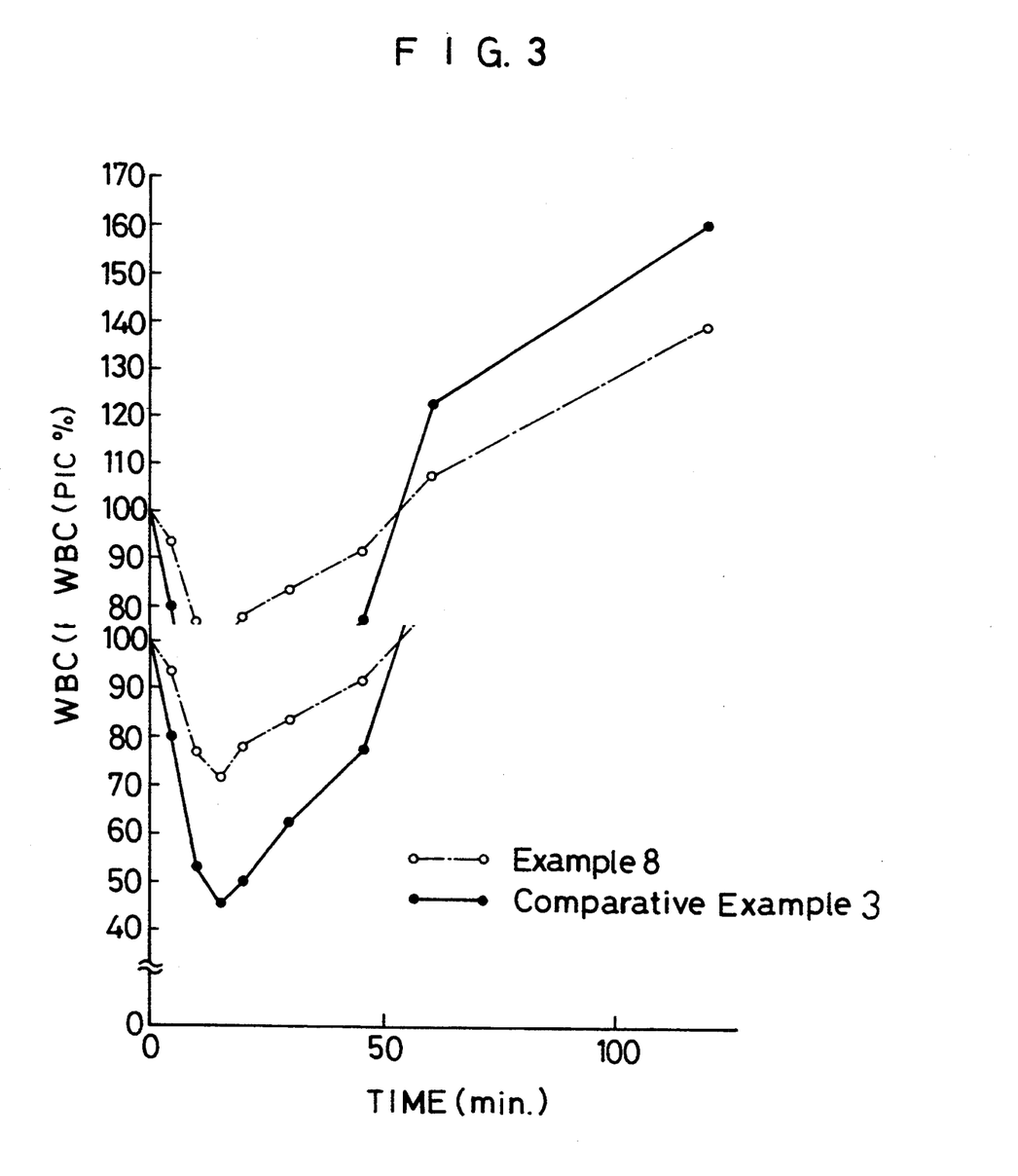
FIG. 3 is a graph showing periodical changes in the number of leukocytes obtained in Example 8 and Comparative Example 3.

Changes in the number of white blood cells are also shown graphically in FIG. 3.

TABLE 4

| Time (min) | WBC cells/mm3 | WBC ratio (%) | PLT cells × 10⁴/mm³ | PLT ratio (%) | HCT (%) | HCT ratio (%) |
| --- | --- | --- | --- | --- | --- | --- |
| 0 | 4200 | 100 | 39.0 | 100 | 43.0 | 100 |
| 5 | 3900 | 93.3 | 36.8 | 94.8 | 42.8 | 99.5 |
| 10 | 3200 | 76.4 | 35.7 | 91.8 | 42.9 | 99.8 |
| 15 | 3000 | 71.4 | 35.2 | 90.3 | 43.0 | 100.0 |
| 20 | 3300 | 77.7 | 34.3 | 86.9 | 43.5 | 101.2 |
| 30 | 3500 | 83.5 | 32.8 | 84.3 | 42.9 | 99.8 |
| 45 | 3800 | 91.5 | 30.8 | 79.9 | 42.5 | 98.8 |
| 60 | 4500 | 107.6 | 29.2 | 75.2 | 42.8 | 99.5 |
| 120 | 5800 | 139.1 | 29.8 | 76.9 | 42.7 | 99.3 |

WBC, white blood cell count; PLT, platelet count; and HCT, hematocrit value.

TABLE 5

| Time (min) | WBC cells/mm3 | WBC ratio (%) | PLT cells × 10⁴/mm³ | PLT ratio (%) | HCT (%) | HCT ratio (%) |
| --- | --- | --- | --- | --- | --- | --- |
| 0 | 4200 | 100 | 45.2 | 100 | 35.2 | 100 |
| 5 | 3300 | 79.5 | 39.8 | 89.1 | 34.8 | 98.9 |
| 10 | 2200 | 52.7 | 36.5 | 81.2 | 35.0 | 99.4 |
| 15 | 1900 | 45.4 | 36.1 | 80.1 | 35.1 | 99.7 |
| 20 | 2100 | 49.9 | 30.2 | 66.6 | 35.3 | 100.3 |
| 30 | 2600 | 62.4 | 28.3 | 63.1 | 34.9 | 99.1 |
| 45 | 3200 | 77.3 | 24.3 | 54.5 | 34.7 | 98.6 |
| 60 | 5100 | 122.5 | 22.3 | 49.8 | 34.9 | 99.1 |
| 120 | 6700 | 160.4 | 21.8 | 48.5 | 35.0 | 99.4 |

WBC, white blood cell count; PLT, platelet count; and HCT, hematocrit value.

Thus, it is apparent that there has been provided, in accordance with the present invention, a medical material in which biocompatibility is provided to a substrate stably for over an extended period of time because of the ability of the material to reduce or prevent undesirable physiological properties inherent in the substrate, such as blood clotting, activation of complement system, platelet adhesion and the like. In addition, the medical material described above can be produced with remarkably high efficiency by the process of the present invention for producing the medical material.

We claim:

1. A blood-compatible medical material comprising:
   a base material (A) comprising at least one member selected from the group consisting of cellulose, polyvinyl alcohol, polyvinyl acetate, copolymers of ethylenevinyl alcohol, copolymers of ethylenevinyl acetate. poly(meth)acrylic acid, chitin, chitosan, collagen, and polyacrylamide;
   a copolymer (B) covalently bonded to said base material having as a component at least one member selected from the group consisting of glycidyl (meth)acrylate, alkyl(meth)acrylate, glycidyl (meth)acrylate-(meth)acrylic acid, (meth)acryloxy alkyl alkoxy silane, (meth)acrylic and alkyl(meth-)acrylic acid; and
   a component selected from the group consisting of a fatty acid ester of a fatty acid and an alkylene glycol or an amide of fatty acid and alkylene diamine, covalently bonded to said copolymer (B).

2. The blood-compatible medical material according to claim 1, wherein said copolymer (B) has a molecular weight of 500 to 500,000.

3. The blood-compatible medical material according to claim 1, wherein said base material is cellulose.

4. The blood-compatible medical material of claim 1, wherein the fatty acid is selected from the group consisting of elaidic acid, oleic acid, linoleic acid, linolenic acid, arachidonic acid, eicosapentaenoic acid, lauric acid, myristic acid, pentadecylic acid, palmitic acid, and stearic acid.

5. The blood-compatible medical material according to claim 4, wherein said fatty acid is linoleic acid.

6. The blood-compatible medical material according to claim 1, wherein said copolymer (B) is a blycidyl(-meth)acrylate copolymer.

7. The blood-compatible medical material according to claim 1, wherein said copolymer (B) is a glycidyl (meth)acrylate-(meth)acrylic acid copolymer.

8. The blood-compatible medical material according to claim 1, wherein said component is an amine of a fatty acid and an alkylene glycol diamine.

9. The blood-compatible medical material according to claim 8, wherein said alkylene glycol diamine is polyethylene glycol diamine or polypropylene glycol diamine.

10. A medical device having a blood contacting member, wherein the blood contacting member comprises the medical material according to claim 1.

* * * * *

UNITED STATES PATENT AND TRADEMARK OFFICE
CERTIFICATE OF CORRECTION

PATENT NO. : 5,336,698
DATED : August 9, 1994
INVENTOR(S) : Nobuyoshi Kashiwagi et al Page 1 of 3

It is certified that error appears in the above-indentified patent and that said Letters Patent is hereby corrected as shown below:

In Column 1, line 36, delete "macromet" and insert -- macromer --.

In Column 1, line 49, delete "to" (first occurrence) and insert -- of --.

In Column 2, line 13, delete "will[be" and insert -- will be --.

In Column 2, line 41, after "point", insert -- of --.

In Column 2, line 61, after "compatibility", insert -- . --.

In Column 2, line 66, delete "biocompatiDility" and insert -- biocompatibility --.

In Column 4, line 26, delete "simultaneousy" and insert -- simultaneously --.

In Column 5, line 8, delete "earrib" and insert -- earth --.

In Column 5, line 55, delete "ramrig;" and insert -- mmHg --.

In Column 6, line 17, delete "(1H-NMR" and insert -- $^1$H-NMR --.

In Column 6, line 31, delete "-C$\underline{H}${C$\underline{H}$-" and insert -- -C$\underline{H}$=C$\underline{H}$- --.

In Column 6, lines 64-65, delete "ethyltrimethylanunoiniumbromide" and insert -- ethyltrimethylammoniumbromide --.

In Column 7, line 51, delete "lit:oleic" and insert -- linoleic --.

In Column 7, line 63, delete "130" and insert -- 30 --.

In Column 8, line 7, delete "anti" and insert -- and --.

UNITED STATES PATENT AND TRADEMARK OFFICE
CERTIFICATE OF CORRECTION

PATENT NO. : 5,336,698
DATED : August 9, 1994
INVENTOR(S) : Nobuyoshi KASHIWAGI et al It is certified that error appears in the above-indentified patent and that said Letters Patent is hereby corrected as shown below:

In Column 8, line 10, delete "flask." and insert -- flask --.

In Column 8, line 22, delete "/fluid" and insert -- fluid --.

In Column 8, line 24, delete "burying" and insert -- drying --.

In Column 8, line 40, delete "Z" and insert -- I --.

In Column 9, line 12, delete ",," and insert -- , --.

In Column 9, line 14, delete "ana" and insert -- and --.

In Column 9, line 16, delete "repealed" and insert -- repeated --.

In Column 9, line 38, after "0.5", insert -- % --.

In Column 9, line 47, after "2", insert -- . --.

In Column 10, line 17, delete "alehydrated" and insert -- dehydrated --.

In Column 11, line 62, delete "34 1" and insert -- 341 --.

In Column 11, line 63, delete "cupraponium" and insert -- cuprammonium --.

In Column 12, line 1, delete "polyurenhane" and insert -- polyurethane --.

In Column 12, line 5, delete "DOtH" and insert -- both --.

In Column 12, line 6, after "circulation", delete ".".

In Column 12, line 6, delete "I" and insert -- 1 --.

In Column 12, line 23, delete "pare or column" and insert -- part of common --.

In Column 12, line 25, after "part", delete ".".

In Column 12, line 32, delete ".." and insert -- . --.

In Column 12, line 57, after "mersed", insert -- in --.

UNITED STATES PATENT AND TRADEMARK OFFICE
CERTIFICATE OF CORRECTION

PATENT NO. : 5,336,698
DATED : August 9, 1994
INVENTOR(S) : Nobuyoshi KASHIWAGI et al It is certified that error appears in the above-indentified patent and that said Letters Patent is hereby corrected as shown below:

In Column 13, line 6, delete "Na2-EDTA" and insert -- $Na_2$-EDTA --.
In Column 14, line 18, delete "." and insert -- , --.
In Column 14, line 23, after "(meth)acrylate," insert
-- glycidyl(meth)acrylate-(meth)acrylic acid--.
In Column 14, line 23, after "alkyl(meth)acrylate", delete "glycidyl".
In Column 14, line 24, delete "(meth)acrylate-(meth)acrylic acid".
In Column 14, line 28, after "acid", insert -- , --.
In Column 14, line 45, delete "blycidyl(-" and insert -- glycidyl(- --.
In Column 14, line 51, delete "amine" and inert -- amide --.

Signed and Sealed this

Eleventh Day of April, 1995

BRUCE LEHMAN

Commissioner of Patents and Trademarks